United States Patent
Wada et al.

(10) Patent No.: US 9,667,843 B2
(45) Date of Patent: May 30, 2017

(54) IMAGING MODULE, INSULATING-TUBE-ATTACHED IMAGING MODULE, LENS-ATTACHED IMAGING MODULE, AND ENDOSCOPE

(71) Applicant: FUJIKURA LTD., Tokyo (JP)

(72) Inventors: Hideyuki Wada, Sakura (JP); Kenichi Nakatate, Sakura (JP)

(73) Assignee: FUJIKURA LTD., Tokyo (JP)

( * ) Notice: Subject to any disclaimer, the term of this patent is extended or adjusted under 35 U.S.C. 154(b) by 0 days.

(21) Appl. No.: 14/761,757

(22) PCT Filed: Feb. 13, 2014

(86) PCT No.: PCT/JP2014/053313
§ 371 (c)(1),
(2) Date: Jul. 17, 2015

(87) PCT Pub. No.: WO2014/126144
PCT Pub. Date: Aug. 21, 2014

(65) Prior Publication Data
US 2015/0365571 A1    Dec. 17, 2015

(30) Foreign Application Priority Data

Feb. 13, 2013 (JP) ................................. 2013-025475

(51) Int. Cl.
*H04N 5/225*     (2006.01)
*G02B 23/26*     (2006.01)
(Continued)

(52) U.S. Cl.
CPC ............ *H04N 5/2252* (2013.01); *A61B 1/051* (2013.01); *G02B 23/2484* (2013.01); *G02B 23/26* (2013.01); *H04N 5/2253* (2013.01)

(58) Field of Classification Search
CPC .... H04N 5/2252; H04N 5/2253; A61B 1/051; G02B 23/2484; G02B 23/26
See application file for complete search history.

(56) References Cited

U.S. PATENT DOCUMENTS

2002/0080233 A1*   6/2002   Irion ................... H04N 5/2251
                                                              348/65
2009/0021618 A1*   1/2009   Schwarz ............. H04N 5/2251
                                                              348/294
(Continued)

FOREIGN PATENT DOCUMENTS

EP       2 719 319 A1    4/2014
JP       62-098318 A    5/1987
(Continued)

OTHER PUBLICATIONS

Communication dated May 10, 2016 from the Japanese Patent Office in counterpart application No. 2015-500282.
(Continued)

*Primary Examiner* — Gevell Selby
(74) *Attorney, Agent, or Firm* — Sughrue Mion, PLLC (57) ABSTRACT

An imaging module of the invention includes: an electrical cable; a solid-state image sensing device; and a three-dimensional wiring base in which a mount surface is provided on a molded product. The mount surface has two opposed apexes which sandwich a central portion therebetween and is molded so that the distance between the two apexes is the longest in distances between two points on sides of the mount surface, a cross section parallel to the mount surface of the three-dimensional wiring base is equal to the mount surface or smaller than the mount surface, and the distance between two points that is the longest in distances on sides of a shape in a plan view of the solid-state image sensing device is equal to or shorter than the distance between the two apexes.

16 Claims, 7 Drawing Sheets

(51) Int. Cl.
  *G02B 23/24* (2006.01)
  *A61B 1/05* (2006.01)

(56) References Cited

U.S. PATENT DOCUMENTS

| | | | |
|---|---|---|---|
| 2011/0249106 A1* | 10/2011 | Makino | H04N 5/2254 348/76 |
| 2012/0104230 A1* | 5/2012 | Eismann | H04N 5/2253 250/208.1 |
| 2013/0258183 A1 | 10/2013 | Kamei | |
| 2014/0009593 A1* | 1/2014 | Segi | H04N 5/2257 348/76 |
| 2014/0249472 A1* | 9/2014 | Mulvihill | A61M 25/00 604/95.01 |

FOREIGN PATENT DOCUMENTS

| | | |
|---|---|---|
| JP | 63-118120 A | 5/1988 |
| JP | 63-155016 A | 6/1988 |
| JP | 2000209472 A | 7/2000 |
| JP | 2001-027734 A | 1/2001 |
| JP | 2008237732 A | 10/2008 |
| JP | 2009027709 A | 2/2009 |
| JP | 2009-201762 A | 9/2009 |
| JP | 2011-240053 A | 12/2011 |
| JP | 2012-254176 A | 12/2012 |
| JP | 2013211629 A | 10/2013 |

OTHER PUBLICATIONS

Communication dated Aug. 23, 2016, from the Japanese Patent Office in counterpart application No. 2015-500282.

* cited by examiner

FIG. 9C

# IMAGING MODULE, INSULATING-TUBE-ATTACHED IMAGING MODULE, LENS-ATTACHED IMAGING MODULE, AND ENDOSCOPE

CROSS-REFERENCE TO RELATED APPLICATION

This is the U.S. National Phase Application under 35 U.S.C. §371 of International Patent Application No. PCT/JP2014/053313 filed Feb. 13, 2014, which designated the United States and was published in a language other than English, which claims the benefit of Japanese Patent Application No. 2013-025475 filed on Feb. 13, 2013, both of them are incorporated by reference herein. The International Application was published in Japanese on Aug. 21, 2014 as WO2014/126144 A1 under PCT Article 21(2).

BACKGROUND OF THE INVENTION

Field of the Invention

The present invention relates to an imaging module configured so that a solid-state image sensing device is packaged on a three-dimensional wiring base, an insulating-tube-attached imaging module configured by using the imaging module, a lens-attached imaging module, and an endoscope.

Description of the Related Art

It is essential for an imaging module used in an endoscope to be small.

The imaging module is configured to include a small solid-state image sensing device such as a CCD (Charge Coupled Device) chip or a CMOS (Complementary Metal Oxide Semiconductor) chip and a wiring base that has a surface on which wirings are formed and is used to package the above-mentioned solid-state image sensing device thereonto.

In the above-described solid-state image sensing device, for example, stacked chips have a configuration in which terminals used to connect a wiring base to the opposite side of a light-receiving face via through-hole interconnections (TSV: Trough Silicon Via) are provided.

On the other hand, as the wiring base on which the solid-state image sensing device is mounted, for example, a three-dimensional wiring base is used.

The three-dimensional wiring base is used to three-dimensionally package electronic components thereon and has a structure in which wirings are formed on a surface of a three-dimensional molded product made of resin, ceramic, or the like.

For example, in an imaging module used in an endoscope, a three-dimensional wiring base is molded in a substantially cylindrical shape, and a circular mount surface is provided on a substantially cylindrical-shaped front end.

For example, imaging modules that are formed by use of the aforementioned solid-state image sensing device and the three-dimensional wiring base and are used in endoscopes, are disclosed in Japanese Unexamined Patent Application, First Publication No. 2001-27734, Japanese Unexamined Patent Application, First Publication No. 2009-201762, Japanese Unexamined Patent Application, First Publication No. 2011-240053, or Japanese Unexamined Patent Application, First Publication No. 2012-254176.

However, in the above-mentioned conventional technologies, the imaging module is covered with the cylindrical insulating tube in order to ensure electrical insulation between surface wirings formed on the three-dimensional wiring base; however, since the mount surface of the three-dimensional wiring base is formed in a circular shape, the entire outer-periphery of the mount surface is caught by the inner surface of the insulating tube at the time of inserting the imaging module into the insulating tube, there is a problem in that it is difficult to insert it into the insulating tube.

Additionally, in the above-mentioned conventional technologies, it is necessary to provide, on the surface of the mount surface, an alignment mark that serves as a mark used to package a solid-state image sensing device on the right position; however, since the mount surface of a three-dimensional wiring base used in an imaging module of an endoscope is extremely small, it is extremely difficult to provide the alignment mark on the mount surface.

SUMMARY OF THE INVENTION

The invention was made in view of the above-described situation, and has an object to cause a solid-state image sensing device to be easily inserted into an insulating tube and to provide an alignment mark used to attach the solid-state image sensing device to the right position.

In order to achieve the object, an imaging module according to a first aspect of the invention includes: an electrical cable; a solid-state image sensing device having a light-receiving face perpendicular to an axis direction of a front end of the electrical cable; and a three-dimensional wiring base in which a wiring is formed on a surface of a molded product extending in the axis direction, the electrical cable is electrically connected to the solid-state image sensing device via the wiring, and a mount surface used to package the solid-state image sensing device thereon is provided on a front end of the molded product, wherein the mount surface has two opposed apexes which sandwich a central portion therebetween and is molded so that the distance between the two apexes is the longest in the distances between two points on sides of the mount surface, a cross section parallel to the mount surface of the three-dimensional wiring base is equal to the mount surface or smaller than the mount surface, and the distance between two points that is the longest in the distances on sides of a shape in a plan view of the solid-state image sensing device is equal to or shorter than the distance between the two apexes.

In the imaging module according to the first aspect of the invention, it is preferable that the mount surface be formed in a hexagonal shape.

In the imaging module according to the first aspect of the invention, it is preferable that the molded product have a first surface and a second surface which are positioned so as to sandwich the molded product therebetween and that one electrical cable be provided on each of the first surface and the second surface.

In the imaging module according to the first aspect of the invention, it is preferable that a bend portion which is formed in an extending direction of the molded product be provided so that the angle thereof is greater than a right angle.

In the imaging module according to the first aspect of the invention, it is preferable that the mount surface be provided with a recess-shaped container that fixes the solid-state image sensing device therein.

In the imaging module according to the first aspect of the invention, it is preferable that the surface of the molded product be provided with a groove portion that is used to accommodate the electrical cable therein and extends in an extending direction of the molded product.

In the imaging module according to the first aspect of the invention, it is preferable that the groove portion includes: a groove opening that is located on the same plane as the surface of the molded product and has the width smaller than the diameter of the electrical cable; and an inner groove that is formed inside the groove portion, has a width larger than the width of the groove opening, and accommodates the electrical cable therein.

In the imaging module according to the first aspect of the invention, it is preferable that the electrical cable include a plurality of built-in electrical cables and that groove portions whose number corresponds to the number of the built-in electrical cables be provided.

In the imaging module according to the first aspect of the invention, it is preferable that the groove portion include: a groove opening that is located on the same plane as the surface of the molded product and has the width smaller than the diameter of the built-in electrical cable; and an inner groove that is formed inside the groove portion, has a width larger than the width of the groove opening, and accommodates the built-in electrical cable therein.

In the imaging module according to the first aspect of the invention, it is preferable that the built-in electrical cable be a coaxial cable that is configured to include an internal conductor, a primary coating layer coating the internal conductor, an external conductor provided around the primary coating layer, and a secondary coating layer coating the external conductor, and that the groove portion be provided with step differences that are along the internal conductor exposed at the front end of the built-in electrical cable, the primary coating layer, and the external conductor.

An insulating-tube-attached imaging module according to a second aspect of the invention includes: the imaging module according to the aforementioned first aspect; and an insulating tube that accommodates the imaging module therein.

A lens-attached imaging module according to a third aspect of the invention includes: a sleeve-shaped metal frame member that accommodates: the three-dimensional wiring base and the solid-state image sensing device of the insulating-tube-attached imaging module according to the aforementioned second aspect; and a lens unit fixed to the solid-state image sensing device.

An endoscope according to a fourth aspect of the invention includes: the lens-attached imaging module according to the aforementioned third aspect; and an insertion portion that accommodates the lens-attached imaging module therein.

Effects of the Invention

According to the aspects of the invention, the imaging module includes the above-mentioned constitution; therefore, when the imaging module is inserted into the insulating tube, since the insulating tube comes into contact with two apexes of the three-dimensional wiring base, the imaging module is easily inserted into the insulating tube.

According to the aspects of the invention, it is possible to simply attach the solid-state image sensing device to the right position on the mount surface by using the two apexes of the mount surface as alignment marks.

BRIEF DESCRIPTION OF THE DRAWINGS

FIG. 3B is a view showing wirings 22a, 22b, 22c, 22d, 22e, 22f, and 22g formed on the mount surface 21a.

DETAILED DESCRIPTION OF THE INVENTION

Figure 1A:
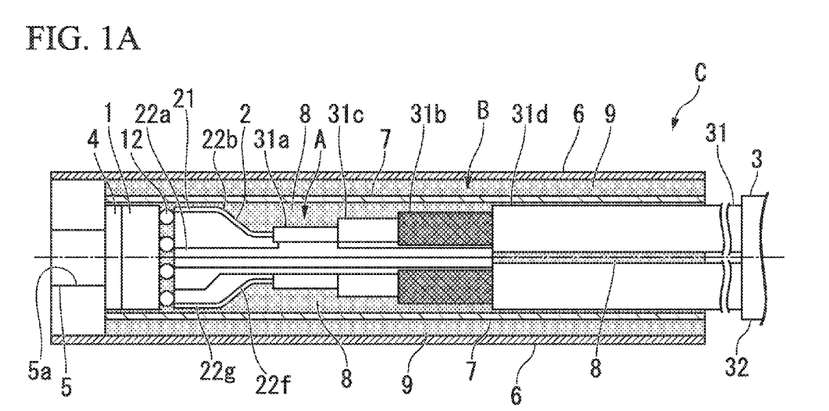
FIG. 1A is a side view showing an imaging module A according to one embodiment of the invention and structures of an insulating-tube-attached imaging module B and a lens-attached imaging module C which are configured by use of the imaging module A.
Figure 1B:
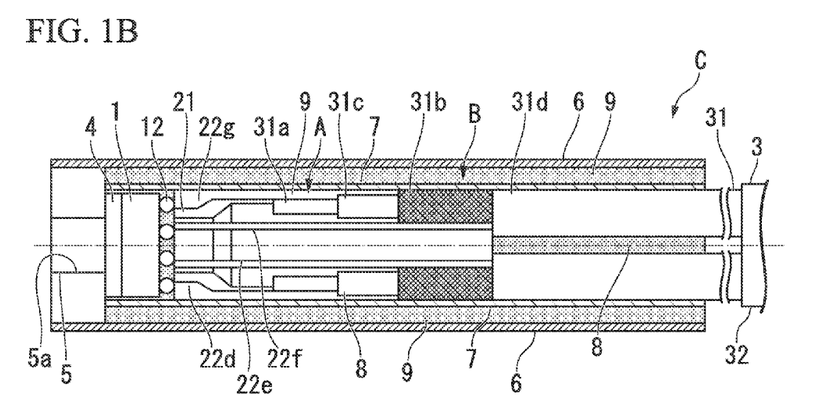
FIG. 1B is a side view showing an imaging module A according to one embodiment of the invention and structures of an insulating-tube-attached imaging module B and a lens-attached imaging module C which are configured by use of the imaging module A.

An imaging module A according to the embodiment is a small image-sensing device used in an endoscope and is configured to include: a solid-state image sensing device 1; three-dimensional wiring base 2; and an electrical cable 3 as shown in FIGS. 1A and 1B.

Moreover, as shown in drawings, such an imaging module A is accommodated in an insulating tube 7 and configures an insulating-tube-attached imaging module B.

Furthermore, as shown in drawings, a lens-attached imaging module C is configured of the aforementioned insulating-tube-attached imaging module B, a cover member 4 that is fixed to the solid-state image sensing device 1, a lens unit 5 (object lens unit), and a metal frame member 6 that is formed in a sleeve-shape such as a cylindrical shape in combination.

The solid-state image sensing device 1 is a semiconductor imaging sensor such as a CCD (Charge Coupled Device) chip or a CMOS (Complementary Metal Oxide Semiconductor) chip, and is fixed on a mount surface 21a of a molded product 21 of the three-dimensional wiring base 2 which will be described later.

The above-described solid-state image sensing device 1 has a top face (light-receiving face) on which a light receiving portion receiving external light is mounted and a back surface that is opposite to the top face.

The solid-state image sensing device 1 is provided with bumps 12 (terminals) such as solder bump which is provided on the back surface and is electrically connected to an electrical circuit provided inside the solid-state image sensing device 1, a stud bump, or a plated bump.

Figure 2:
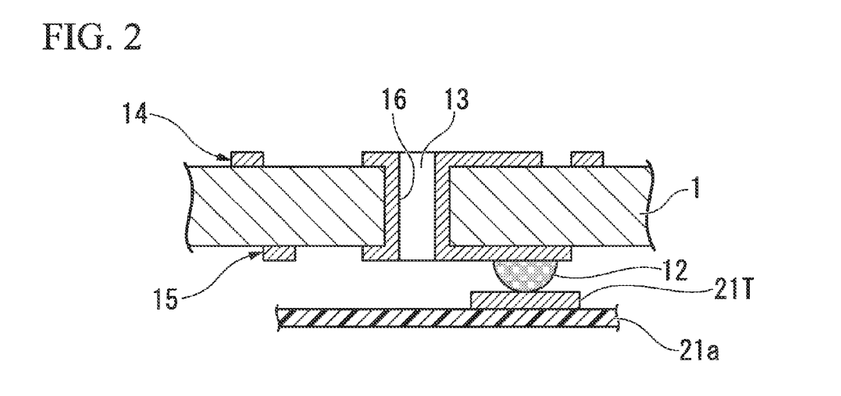
FIG. 2 is a cross-sectional view showing a configuration which is adjacent to a mount surface 21a of a three-dimensional wiring base 2 according to one embodiment of the invention.

For example, as shown in FIG. 2, the solid-state image sensing device 1 includes a through-hole interconnection 16 (through-hole wiring) that is formed inside a through hole 13 penetrating through the solid-state image sensing device 1 in the plate-thickness direction thereof and is electrically connected to wirings 14 and 15 provided on both the top and back surfaces of the solid-state image sensing device 1.

Moreover, as the solid-state image sensing device used in the embodiment, a back-side Illumination CMOS image sensor (BSI: Back-side Illumination type) may be used.

Similarly, in the back-side Illumination CMOS image sensor, a wiring can be drawn via the through-hole interconnection to the surface that is opposite to the light-receiving face.

Furthermore, by a flip-chip method, via the bump 12, the solid-state image sensing device 1 is connected and fixed to a terminal 21T (refer to FIG. 2) formed on the mount surface 21a of the three-dimensional wiring base 2.

The solid-state image sensing device 1 is electrically connected to wirings 22a, 22b, 22c, 22d, 22e, 22f, and 22g the three-dimensional wiring base 2 which will be described later, and is mounted on the mount surface 21a of the three-dimensional wiring base 2.

The three-dimensional wiring base 2 is a wiring base that is used to stereoscopically package an electronic component thereonto, and is constituted of seven wirings 22a, 22b, 22c, 22d, 22e, 22f, and 22g formed on the molded product 21 or the surface of the molded product 21. The molded product is made of a resin (PEEK (polyetheretherketone), LCP (Liquid Crystal Polymer)), ceramic, or the like, which have a heat resistance with respect to heat generated when soldering is carried out.

Particularly, the aforementioned soldering is carried out when the wirings 22a, 22b, 22c, 22d, 22e, 22f, and 22g are connected to the electrical cable 3.

As described above, the above-mentioned molded product 21 is made of a resin (a PEEK material or an LCP material), ceramic, or the like, which have a heat resistance with respect to heat generated when soldering is carried out, and is molded by use of a die or the like.

The foregoing molded product 21 is formed in a shape that extends in the axis direction (a direction perpendicular to the mount surface 21a which will be described later) of a built-in electrical cable 31 exposed at the front end of the electrical cable 3 which will be described later.

Figure 3A:
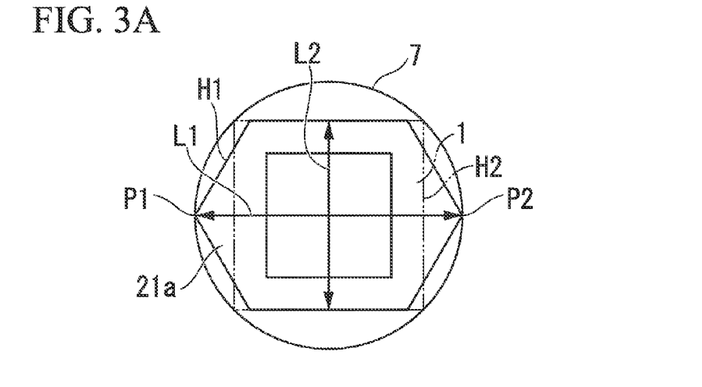
FIG. 3A is a view showing a shape of the mount surface 21a of the three-dimensional wiring base 2 according to one embodiment of the invention.
Figure 3B:
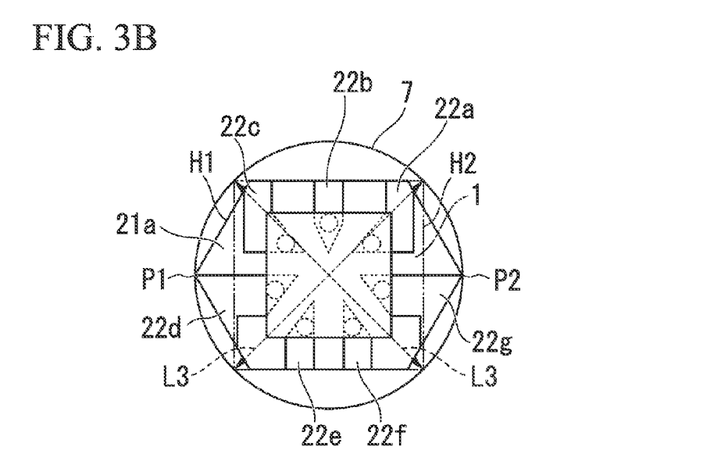

Additionally, regarding the molded product 21, the mount surface 21a on which the solid-state image sensing device 1 is to be mounted is molded in a hexagonal shape as shown in FIGS. 3A and 3B.

Figure 4A:
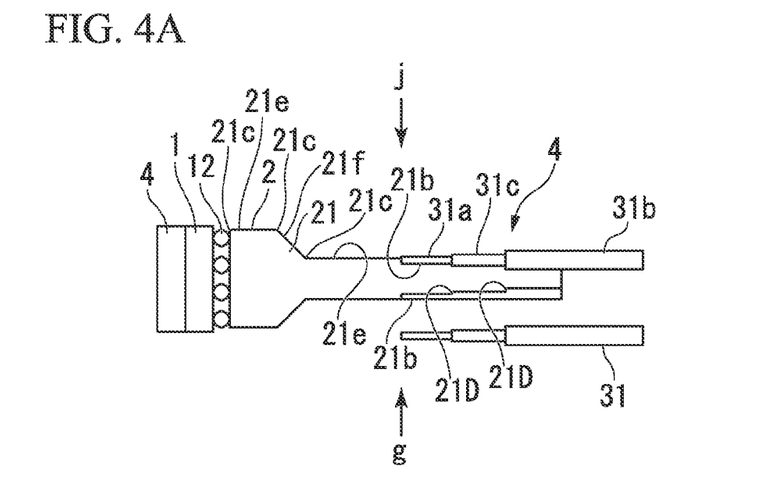
FIG. 4A is a schematic view showing a groove portion 21b formed on a molded product 21 of the three-dimensional wiring base 2 according to one embodiment of the invention.
Figure 4B:
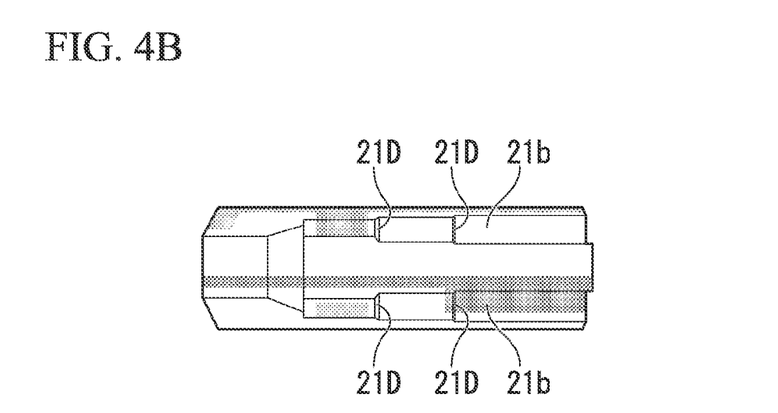
FIG. 4B is a schematic view showing a groove portion 21b formed on a molded product 21 of the three-dimensional wiring base 2 according to one embodiment of the invention and is a view showing the groove portion 21b as seen in the j direction.
Figure 4C:
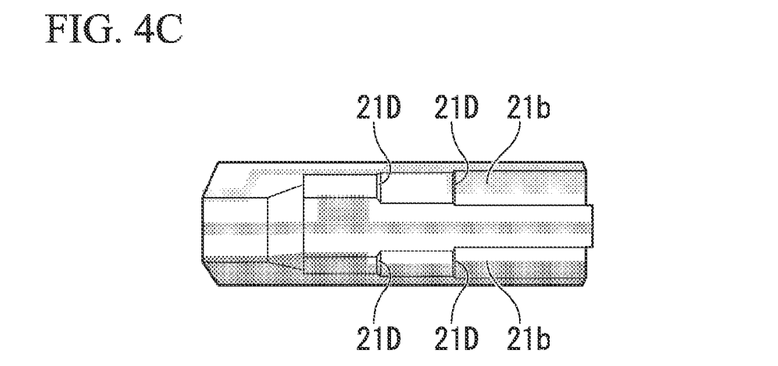
FIG. 4C is a schematic view showing a groove portion 21b formed on a molded product 21 of the three-dimensional wiring base 2 according to one embodiment of the invention and is a view showing the groove portion 21b as seen in the g direction.

Furthermore, as shown in FIGS. 4A to 4C, four groove portions 21b are provided on the surface of the molded product 21 along the extending direction of the molded product 21 and are used to accommodate the built-in electrical cable 31 of the electrical cable 3 described later therein.

On the other hand, the seven wirings 22a to 22g are provided on the surface of the molded product 21.

Each of the above-described wirings 22a to 22g has a first end and a second end.

Particularly, one of ends (first end) provided on the mount surface 21a is the terminal 21T (FIG. 2) that is connected to the solid-state image sensing device 1, and the other of ends (second end) is the terminal that is connected to the built-in electrical cable 31 of the electrical cable 3 which will be described later.

That is, the solid-state image sensing device 1 is electrically connected to the electrical cables 31 with the wirings 22a to 22g interposed therebetween.

In addition, regarding the wirings 22a to 22g, the portions other than the terminals are coated with a resin having electrical insulation.

Moreover, the three-dimensional wiring base 2 including the aforementioned molded product 21 and the wirings 22a to 22g will be particularly described below.

Figure 5:
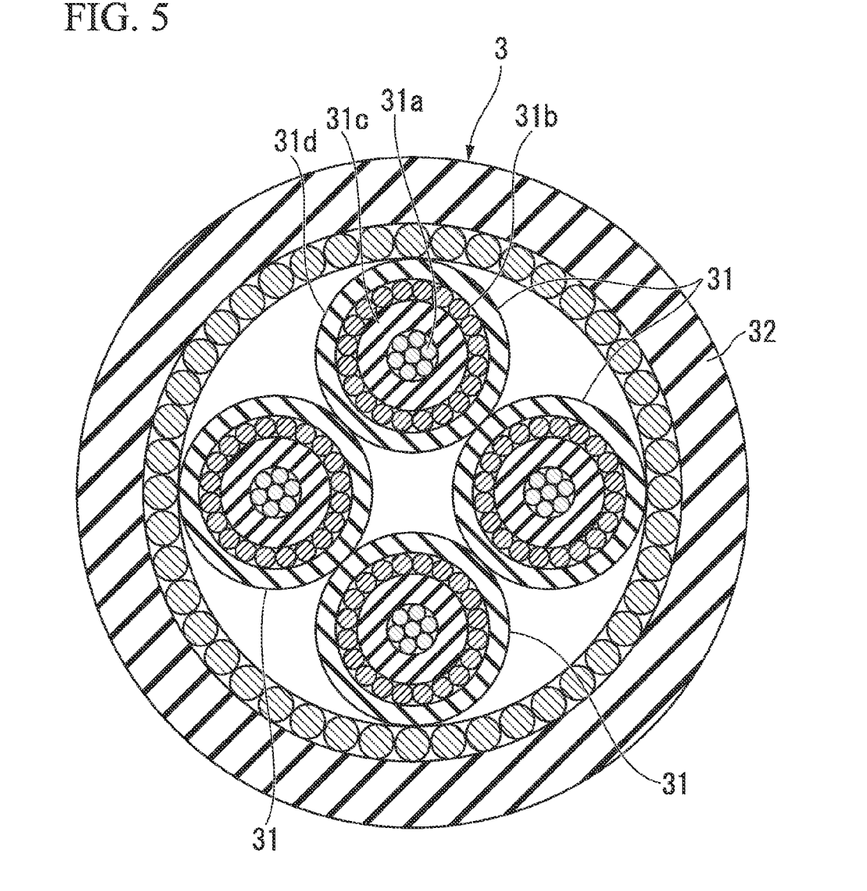
FIG. 5 is a view showing an example of a cross-section structure of the electrical cable 3 according to one embodiment of the invention.

The electrical cable 3 is used to electrically connect an external device (for example, a display device or the like, not shown in the figure) to the solid-state image sensing device 1 and is a cable unit includes a plurality of built-in electrical cables 31 (four cables shown as an example in the drawing) and an outer coating 32 as shown in FIG. 5.

The built-in electrical cable 31 is a coaxial cable and is configured to include an internal conductor 31a, a primary coating layer 31c that coats the internal conductor 31a, an external conductor 31b that is formed of a metal thin wire and is provided around the primary coating layer 31c, and a secondary coating layer 31d that coats the external conductor 31b.

The above-described built-in electrical cable 31 is exposed at the outer coating 32 and at the front end of the electrical cable 3.

Additionally, as shown in FIGS. 1A and 1B, the internal conductor 31a, the primary coating layer 31c, and the external conductor 31b are exposed at the front end of the built-in electrical cable 31 which is exposed at the outer coating 32.

The internal conductor 31a and the external conductor 31b of the foregoing four built-in electrical cables 31 are connected to any of the aforementioned wirings 22a to 22g.

As a result, the solid-state image sensing device 1 is electrically connected to the electrical cable 31 via the wirings 22a to 22g.

Moreover, the internal conductor 31a and the external conductor 31b of the built-in electrical cable 31 are connected to the wirings 22a to 22g by solder or an electro-conductive adhesive which is not shown in the figure.

In contrast, the outer coating 3 is made of a predetermined resin and collectively coats a plurality of the built-in electrical cables 31.

The insulating tube 7 is provided to electrically insulate, from the outside thereof, connectors that connect the wirings 22a to 22g to the internal conductor 31a and the external conductor 31b of the built-in electrical cables 31.

The insulating tube 7 accommodates the imaging module A therein as shown in drawings.

Furthermore, the insulating tube 7 is integrally fixed to the solid-state image sensing device 1, the three-dimensional wiring base 2, and the built-in electrical cables 31, which are provided thereinside, by use of a resin 8 that is cured and fills the inside thereof.

Consequently, the connectors that connect the wirings 22a to 22g to the internal conductor 31a and the external conductor 31b of the built-in electrical cables 31 are not in contact with the metal frame member 6 and are not short-circuited thereto.

The cover member 4 is a plate-shaped transparent member that covers the light receiving portion of the solid-state image sensing device 1.

For example, the cover member 4 is a transparent plate-shaped member made of a glass or a resin.

The lens unit 5 has a structure in which an object lens (not shown in the figure) is incorporated into a cylindrical lens barrel 5a.

The lens unit 5 is positionally-fixed to the optical axis of the light receiving portion of the solid-state image sensing device 1 and is provided so that one end of the lens barrel 5a in the axis direction thereof is fixed to the cover member 4.

The lens unit 5 is configured to provide an image on the light receiving portion of the solid-state image sensing device 1 by guiding light from the opposite side of the cover member 4 through the lenses inside the lens barrel 5a.

The metal frame member 6 is adhesively-fixed to the insulating tube 7 by a resin 9 that is cured and fills the inside of the metal frame member 6.

The foregoing metal frame member 6 accommodates not only the solid-state image sensing device 1 and the three-dimensional wiring base 2 of the imaging module A but also the built-in electrical cables 31 therein.

Particularly, the portion covered with the outer coating 3 of the electrical cable 1 is disposed outside the metal frame member 6. On the other hand, the built-in electrical cables 31 which are exposed at the outer coating 3 of the electrical cable 1 are drawn into the metal frame member 6.

Figure 6:
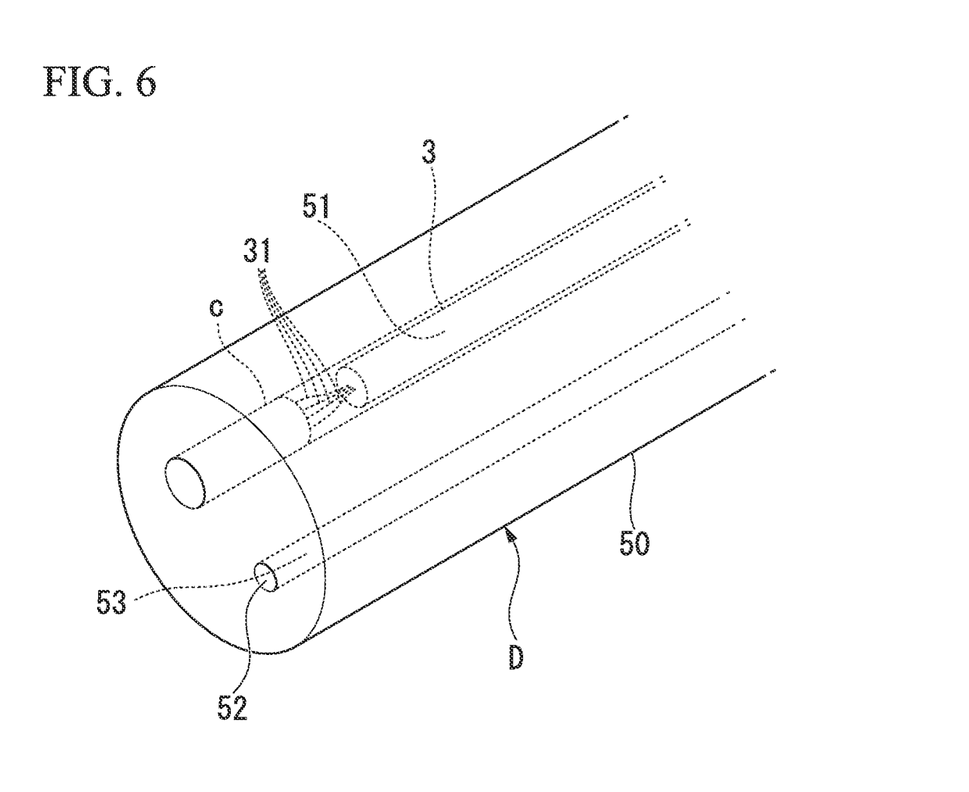
FIG. 6 is a view explaining an endoscope D according to one embodiment of the invention and is an enlarged perspective view showing the tube end thereof.

Additionally, the aforementioned insulating-tube-attached imaging module B and an insertion portion 50 that accommodates the insulating-tube-attached imaging module B therein, in combination, configure an endoscope D.

The aforementioned endoscope D is configured to include: a lumen 51 (first lumen) in the insertion portion 50 that accommodates the lens-attached imaging module B therein; and a lumen 53 (second lumen) that accommodates an optical fiber 52 for illuminating light (light guide).

As a specific example of the lens-attached imaging module, a lens-attached imaging module C was manufactured as a prototype by use of a flat plate-shaped solid-state image sensing device 1 having 0.75 mm square, a three-dimensional wiring base 2 of which the mount surface 21a has a maximum width of 1.00 mm or less, an insulating tube 7 made of silicone and having an outer diameter of 1.05 mm, a cylindrical metal frame member 6 having an outer diameter of 1.2 mm.

Moreover, an outer diameter of the insertion portion of the endoscope D that is manufactured as a prototype by use of the lens-attached imaging module C was 5 mm.

Next, the three-dimensional wiring base 2 of the imaging module A will be particularly described.

Firstly, a manufacturing process of the three-dimensional wiring base 2 will be described.

In the manufacturing process, initially, the molded product 21 is formed.

That is, as a result of causing a resin (a PEEK material or an LCP material), ceramic, or the like, which have a heat resistance with respect to heat generated when soldering is carried out, to flow into a die used to cast the molded product 21, the molded product 21 having a predetermined shape is formed.

Additionally, the entire surface of the molded product 21 is plated by copper (Cu), and the three-dimensional wiring base 2 is manufactured by drawing a wiring pattern by laser.

The three-dimensional wiring base 2 according to the embodiment which is manufactured through the above-mentioned manufacturing process has three distinct configurations.

The first characteristic point is as follows.

The mount surface 21a of the three-dimensional wiring base 2 on which the solid-state image sensing device 1 is to be mounted is molded in a hexagonal shape as shown in FIGS. 3A and 3B.

On the above-described mount surface 21a, the distance between two apexes P1 and P2 of six apexes of the hexagonal shape, which are opposed to each other so as to sandwich the center portion, is the longest in the distances between two points located on the sides H1 of the mount surface 21a.

That is, the line segment L1 between the apexes P1 and P2 is the longest in the line segments that are present on the mount surface 21a and includes the diagonal line between other apexes, the line segment L2 orthogonal to the line segment L1 shown in FIG. 3A, or the like.

Furthermore, a cross-sectional face parallel to the mount surface 21a of the three-dimensional wiring base 2 is equal to the mount surface 21a or smaller than the mount surface 21a.

That is, the three-dimensional wiring base 2 is formed in a shape that has the mount surface 21a serving as the front end thereof and extends in a direction vertical to the mount surface 21a so that the peripheral surface of the three-dimensional wiring base 2 does not protrude from the region of the mount surface 21a when seen in a plan view of the mount surface 21a.

Furthermore, in the solid-state image sensing device 1, the longest distance between two points on the side H2 of the shape of the solid-state image sensing device 1 in a plan view is equal to or shorter than that between the two apexes P1 and P2 of the mount surface 21a.

In short, the diagonal line L3 between the apexes of the shape (tetragon) in a plan view of the solid-state image sensing device 1 shown in FIG. 3B is equal to or shorter than that between the two apexes P1 and P2 of the mount surface 21a.

As described above, the mount surface 21a has two opposed apexes P1 and P2 which sandwich the central portion therebetween and is molded so that the line segment between two apexes P1 and P2 is the longest in line segments on the mount surface 21a; the cross section parallel to the mount surface 21a of the three-dimensional wiring base 2 is equal to the mount surface 21a or smaller than the mount surface; and the line segment of the shape of the solid-state image sensing device 1 in a plan view is shorter than that between the two apexes P1 and P2 of the mount surface 21a.

Consequently, when the imaging module A is inserted into the insulating tube 7, the insulating tube 7 is in a state of being in contact with the two apexes P1 and P2 of the three-dimensional wiring base 2; that is, since the region which comes into contact with the insulating tube 7 is narrow, the imaging module A is easily inserted into the insulating tube 7.

Next, the distinct configuration according to the second characteristic point regarding the three-dimensional wiring base 2 will be described.

The molded product 21 of the three-dimensional wiring base 2 has a linear portion 21e that extends in the extending direction thereof and an inclined portion 21f inclined with respect to the linear portion 21e.

An angle of a bend portion 21c of the molded product 21 that is formed in the extending direction (angle between the linear portion 21e and the inclined portion 21f) is greater than the right angle.

That is, the bend portion 21c is not formed at a sharp angle such as 90 degrees or less and is formed at an obtuse angle such as 90 degrees or more.

As a result, since the wirings 22a to 22g that are arranged in the extending direction of the three-dimensional wiring base 2 are not bent at a sharp angle such as the right angle or less, it is possible to prevent wire breakage.

Next, the distinct configuration according to the third characteristic point regarding the three-dimensional wiring base 2 will be described.

The groove portions 21b are provided on the surface of the molded product 21 and extend in the extending direction of the molded product 21 to accommodate the electrical cable 3 therein.

That is, the groove portions 21b are provided so that the number thereof (four) corresponds to that of the built-in electrical cables 31.

Moreover, as shown in FIGS. 4A to 4C, in the groove portion 21b, step differences 21D are provided so as to correspond to the configuration of the internal conductor 31a that is exposed at the front end of the built-in electrical cable 31 and to the configurations of the primary coating layer 31c and the external conductor 31b.

Consequently, it is possible to attach the built-in electrical cables 31 to the right position on the three-dimensional wiring base 2.

Moreover, since the built-in electrical cables 31 can be easily attached to the three-dimensional wiring base 2 by the aforementioned configuration, it is possible to omit time and effort during attachment.

In the above-described embodiment, the mount surface 21a has two opposed apexes P1 and P2 which sandwich the central portion therebetween and is molded so that the line segment between two apexes P1 and P2 is the longest in line segments on the mount surface 21a; the cross section parallel to the mount surface 21a of the three-dimensional wiring base 2 is equal to the mount surface 21a or smaller than the mount surface; and the line segment of the shape of the solid-state image sensing device 1 in a plan view is shorter than that between the two apexes P1 and P2 of the mount surface 21a.

Because of this, when the imaging module A is inserted into the insulating tube 7, the insulating tube 7 is in a state of being in contact with the two apexes P1 and P2 of the three-dimensional wiring base 2; that is, since the surface area which comes into contact with the insulating tube 7 is smaller than that of a conventionally cylindrical-shaped three-dimensional wiring base, the imaging module A is easily inserted into the insulating tube 7.

In order to mount the solid-state image sensing device 1 onto the mount surface 21a of the three-dimensional wiring base 2 with a high level of positional accuracy, an alignment mark is formed on the mount surface 21a in advance, and it is necessary to carry out the mounting step while adjusting the positional relationship between the alignment mark and the solid-state image sensing device 1.

However, in the case of providing the alignment mark on the mount surface 21a, it is necessary to make the three-dimensional wiring base 2 larger by the amount of the space on which the alignment mark is formed.

According to the embodiment, the two apexes P1 and P2 on the mount surface 21a can be used as the alignment mark.

For this reason, without providing an alignment mark on the mount surface 21a, it is possible to attach the solid-state image sensing device 1 to the right position on the mount surface 21a.

In addition, according to the embodiment, since the molded product 21 is provided so that the angle of the bend portion 21c formed in the extending direction is greater than the right angle, the wirings 22a to 22g that are provided along the extending direction of the three-dimensional wiring base 2 are not bent at a sharp angle such as a right angle or less.

As a result, it is possible to prevent wire breakage.

Furthermore, according to the embodiment, the groove portions 21b are provided and extend in the extending direction of the molded product 21 to accommodate the built-in electrical cables 31 therein.

Consequently, it is possible to attach the built-in electrical cables 31 to the right position on the three-dimensional wiring base 2; in addition to this, since the built-in electrical cables 31 can be easily attached to the three-dimensional wiring base 2, it is possible to omit time and effort during attachment.

As described above, the embodiment of the invention is explained; however, the invention is not limited to the above-mentioned embodiment, for example, the following modification is conceivable.

The endoscope D according to the embodiment of the invention accommodates the imaging module A along with the lens unit 5 fixed to the solid-state image sensing device 1 in the sleeve-shaped metal frame member 6.

As long as the imaging module is the imaging module according to the embodiment of the invention, it is not particularly limited.

Additionally, the mount surface 21a is molded in a hexagonal shape in the embodiment, the invention is not limited to this.

As long as the mount surface 21a is compliant with the aforementioned conditions, a polygonal shape other than a hexagonal shape may be adopted and a shape other than a polygonal shape may be adopted.

Moreover, the step differences 21D that are along the shapes of the internal conductor 31a, the primary coating layer 31c, and the external conductor 31b are provided in the groove portion 21b in the embodiment; however, the step differences 21D may not be provided.

For example, the internal conductor 31a, the primary coating layer 31c, and the external conductor 31b may be pressed into and accommodated in groove portions 21b in which the step differences 21D are not provided.

Furthermore, the groove portion 21b may be designed to receive the electrical cable 3 that accommodates the built-in electrical cables 31 therein.

Modified Example

Next, modified examples of the above-described embodiment will be described with reference to FIGS. 7 to 9C.

FIGS. 7 to 9C, identical reference numerals are used for the elements which are identical to those of the aforementioned embodiment, and the explanations thereof are omitted or simplified here.

Figure 7:
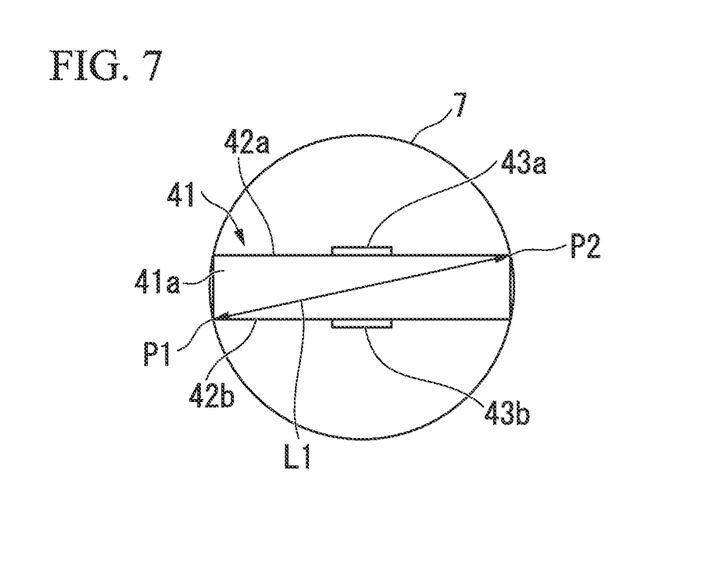
FIG. 7 is a view showing a configuration of a mount surface serving as a modified example according to the embodiment of the invention.

In a modified example shown in FIG. 7, the shape of a mount surface 41a is a rectangular shape, and a molded product 41 is formed in a plate shape.

Specifically, the molded product 41 has a first surface 42a and a second surface 42b located on the opposite side of the first surface 42a, which are located so as to sandwich the molded product 41 therebetween.

One electrical cable is provided on each of the first surface 42a and the second surface 42b.

That is, an electrical cable 43a is provided on the first surface 42a, and an electrical cable 43b is provided on the second surface 42b.

A bump of the solid-state image sensing device is connected and fixed to a terminal which is formed on the mount surface as shown in FIG. 2.

The solid-state image sensing device is electrically connected to the electrical cables 43a and 43b which are provided on the first surface 42a and the second surface 42b, respectively, and the image sensing device is mounted on the mount surface 41a.

In other cases, a groove portion that accommodates a built-in electrical cable of an electrical cable therein may be provided on the first surface 42a and the second surface 42b in the extending direction of the molded product 41.

Figure 8:
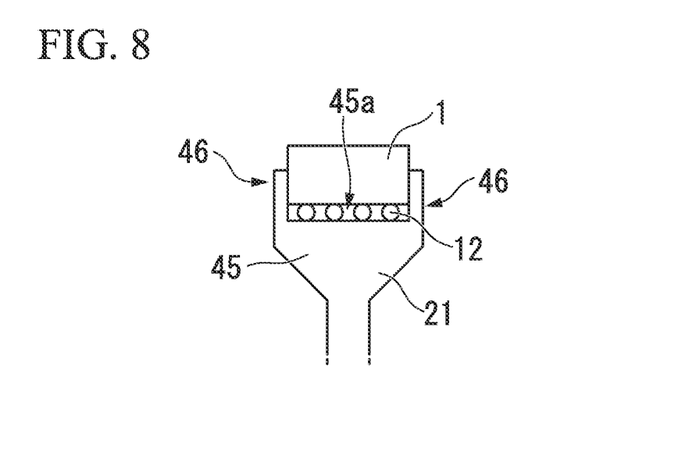
FIG. 8 is a cross-sectional view showing a container serving as a modified example according to the embodiment of the invention which fixes a solid-state image sensing device therein.

In a modified example shown in FIG. 8, a recess-shaped container 46 that causes the solid-state image sensing device 1 to be fixed to a mount surface 45a of a molded product 45 is provided.

The container 46 is provided on the mount surface 45a so as to surround the solid-state image sensing device 1; as the solid-state image sensing device 1 is disposed inside the container 46, the positioning of the solid-state image sensing device 1 is carried out, and the terminal 21T formed on the mount surface 45a is reliably connected to the bump 12 of the solid-state image sensing device 1 (refer to FIG. 2).

In other cases, a wiring extending from the terminal 21T toward the electrical cable may be formed along the surface of the container 46 and may be connected to the electrical cable through a cut-off portion that is partially provided on the container 46.

Moreover, FIG. 8 shows a structure in which part of the container 46 (outer surface) forms the external face of the molded product 45; however, the invention is not limited to the above-described configuration.

For example, a container may be formed between the wirings 22a and 22b, between the wirings 22b and 22c, between the wirings 22d and 22e, and between the wirings 22f and 22g which are shown in FIG. 3B so as to protrude from the mount surface.

In other words, a container may be formed between wirings adjacent to each other formed on the mount surface.

In this case, it is preferable that the solid-state image sensing device 1 be in contact with the container at at least three portions and that the position of the solid-state image sensing device 1 be aligned.

Figure 9A:
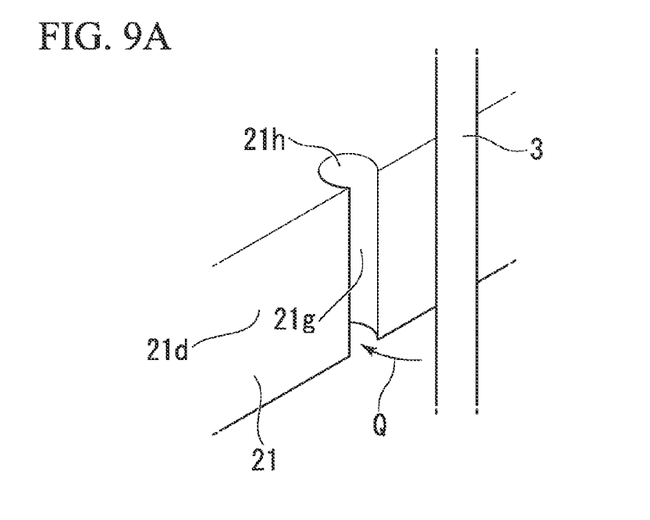
FIG. 9A is a perspective view showing a groove serving as a modified example according to the embodiment of the invention which fixes an electrical cable therein.
Figure 9B:
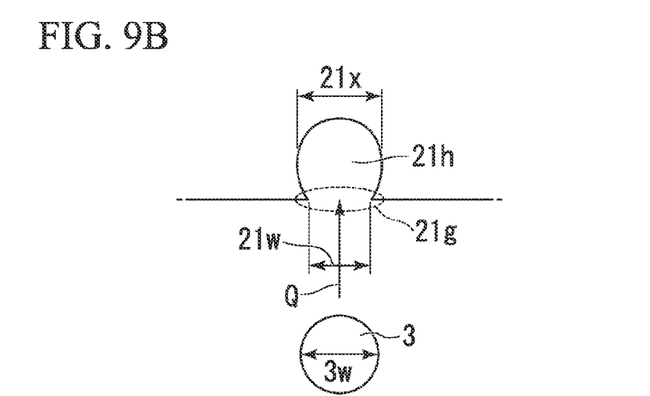
FIG. 9B is a cross-sectional view showing a groove serving as a modified example according to the embodiment of the invention which fixes an electrical cable therein and is a view showing a state before the electrical cable is inserted into the groove.
Figure 9C:
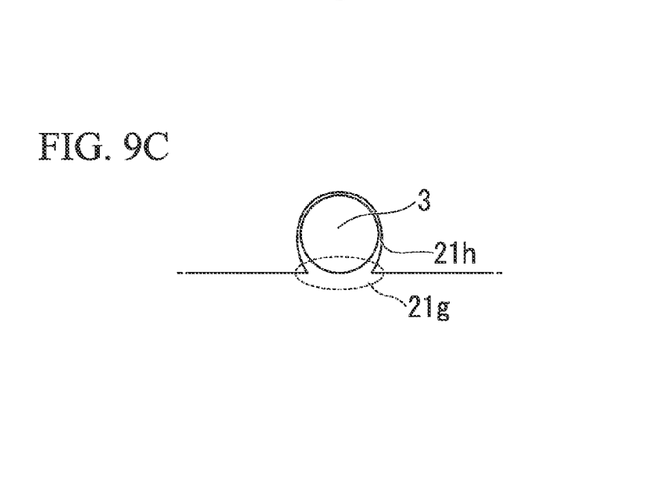
FIG. 9C is a cross-sectional view showing a groove serving as a modified example according to the embodiment of the invention which fixes an electrical cable therein and is a view showing a state after the electrical cable is inserted into the groove.

FIGS. 9A to 9C show a modified example of the groove portion 21b that is provided along the extending direction of the molded product 21.

In the modified example described below, "width" means a length in a direction orthogonal to the extending direction of the groove portion 21b, "width direction" means a direction orthogonal to the extending direction of the groove portion 21b.

The groove portion 21b has a groove opening 21g and an inner groove 21h and is formed on the surface 21d of the molded product 21.

The groove opening 21g is located on the same plane as the surface 21d of the molded product 21.

The inner groove 21h opens at the groove opening 21g and is formed inside the groove portion 21b.

The width 21w of the groove opening 21g (distance between ends of the groove opening 21g) is smaller than the width 3w of the electrical cable 3 (diameter).

Furthermore, the width 21x of the inner groove 21h is larger than the width 21w of the groove opening 21g.

Here, the width 21w of the groove opening 21g is set to the width of the electrical cable 3 when the electrical cable 3 is constricted by elastic deformation in the width direction.

That is, the width 21w is substantially equal to the width of the electrical cable 3 which is obtained when the diameter thereof is reduced by elastic deformation.

Additionally, the width 21x of the inner groove 21h is determined based on the width 3w of the electrical cable 3 so that the electrical cable 3 can be accommodated in the groove portion 21b.

For example, the width 21x of the inner groove 21h may be substantially the same as the width 3w that is obtained after the elastically-deformed electrical cable 3 is restored to the original state inside the inner groove 21h.

Moreover, in order to stably hold the electrical cable 3 in the inner groove 21h, the width 21x may be slightly smaller than the width 3w.

As shown in FIG. 9A showing a perspective view and FIG. 9B showing a cross-sectional view, when the electrical cable 3 is inserted into the inner groove 21h through the groove opening 21g, the electrical cable 3 is pressed onto the surface 21d so as to face the groove portion 21b in the direction indicated by reference letter Q.

Since the width 3w is larger than the width 21w, when the electrical cable 3 comes into contact with the ends of the groove opening 21g and is pressed toward the inner groove 21h, the electrical cable 3 is elastically deformed while being pressed by the ends of the groove opening 21g, and the width 3w is reduced.

Thereafter, the electrical cable 3 passes through the groove opening 21g and reaches the inner groove 21h, and an elastic deformation state of the electrical cable 3 is released.

As shown in FIG. 9C showing a cross-sectional view, in the inner groove 21h, the shape of the electrical cable 3 is restored to the original state, and the electrical cable 3 is accommodated in the inner groove 21h.

In this state, since the width 21w of the groove opening 21g is smaller than the width 3w of the electrical cable 3, the electrical cable 3 is prevented from being removed from the inner groove 21h.

In the aforementioned modified example, FIG. 9C shows a state where the electrical cable 3 is accommodated in the inner groove 21h; however, part of the electrical cable 3 may protrude from the groove opening 21g while a holding state of the electrical cable 3 is maintained.

Furthermore, as shown in FIGS. 9B and 9C, the shape of the inner groove 21h is a substantially circular shape (a shape in which a circle is cut-off by the groove opening 21g); however, it is not limited to this shape, and a rectangular shape may be adopted.

The shape and the dimensions of the inner groove 21h are suitably determined based on the shape and the dimensions of the electrical cable 3 or depending on a holding state of the electrical cable 3.

Additionally, the groove opening 21g having the width 21w smaller than the width 21x of the inner groove 21h is not necessarily formed on the entire formation area of the groove portion 21b.

This means that, it is only necessary to partially form a plurality of groove opening 21g along the formation area of the groove portion 21b (extending direction).

In this case, the groove openings 21g may be formed at suitable positions in the extending direction of the groove portion 21b so that the electrical cable 3 is prevented from being removed from the inner groove 21h.

The space between the formed groove openings 21g may be an equal interval.

Furthermore, the groove opening 21g may be formed at the position at which the electrical cable 3 is easily removed from the groove portion 21b.

In the above-mentioned embodiment, the groove portions 21b are provided in the extending direction of the molded product 21 so that the number thereof (four) corresponds to that of the built-in electrical cables 31.

The invention is not limited to the above-described configuration, the built-in electrical cable 31 may be provided in the groove portion 21b having the groove opening 21g and the inner groove 21h shown in FIGS. 9A to 9C.

In this case, instead of the electrical cable 3 shown in FIGS. 9A to 9C, the built-in electrical cable 31 is inserted into the inner groove 21h through the groove opening 21g, and the built-in electrical cable 31 is held by the inner groove 21h.

Here, the inner groove 21h opens at the groove opening 21g and is formed inside the groove portion 21b.

The width 21w of the groove opening 21g (the distance between the ends of the groove opening 21g) is smaller than the width (diameter) of the built-in electrical cable 31.

Additionally, the width 21x of the inner groove 21h is larger than the width 21w of the groove opening 21g.

In this state, since the width 21w of the groove opening 21g is smaller than the width of the built-in electrical cable 31, the built-in electrical cable 31 is prevented from being removed from the inner groove 21h.

While preferred embodiments of the invention have been described and shown above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An imaging module comprising:
an electrical cable;
a solid-state image sensing device having a light-receiving face perpendicular to an axis direction of a front end of the electrical cable; and
a three-dimensional wiring base including a molded product extending in the axis direction, the molded product having a surface on which a wiring is formed, the molded product having a mount surface that is used to package the solid-state image sensing device thereon and is provided on a front end of the molded product, the three-dimensional wiring base comprising:
a first linear portion that is connected to the mount surface via a first bend portion;
an inclined portion that is connected to the first linear portion via a second bend portion and is inclined with respect to the first linear portion; and
a second linear portion that is connected to the inclined portion via a third bend portion, the wiring being formed on the first linear portion, the inclined portion, and the second linear portion, the wiring electrically connecting the electrical cable and the solid-state image sensing device, wherein
the mount surface has two opposed apexes which sandwich a central portion therebetween and is molded so that a distance between the two apexes is the longest in distances between two points on sides of the mount surface, a cross section parallel to the mount surface of the three-dimensional wiring base is equal to the mount surface or smaller than the mount surface, and a distance between two points that is the longest in distances on sides of a shape in a plan view of the solid-state image sensing device is equal to or shorter than the distance between the two apexes.

2. The imaging module according to claim 1, wherein the mount surface is formed in a hexagonal shape.

3. The imaging module according to claim 1, wherein the molded product has a first surface and a second surface which are positioned so as to sandwich the molded product therebetween, and one electrical cable is provided on each of the first surface and the second surface.

4. The imaging module according to claim 1, wherein the third bend portion which is located between the inclined portion and the second linear portion and is formed in an extending direction of the molded product is provided so that an angle of the third bend portion is greater than a right angle.

5. The imaging module according to claim 4, wherein the mount surface is provided with a recess-shaped container that fixes the solid-state image sensing device therein.

6. The imaging module according to claim 1, wherein the surface of the molded product is provided with a groove portion that is used to accommodate the electrical cable therein and extends in an extending direction of the molded product.

7. The imaging module according to claim 6, wherein the groove portion comprises:
a groove opening that is located on the same plane as the surface of the molded product and has a width smaller than a diameter of the electrical cable; and
an inner groove that is formed inside the groove portion, has a width larger than a width of the groove opening, and accommodates the electrical cable therein.

8. The imaging module according to claim 6, wherein the electrical cable includes a plurality of built-in electrical cables, and
groove portions whose number corresponds to the number of the built-in electrical cables are provided.

9. The imaging module according to claim 8, wherein the groove portion comprises:
a groove opening that is located on the same plane as the surface of the molded product and has a width smaller than a diameter of the built-in electrical cable; and
an inner groove that is formed inside the groove portion, has a width larger than a width of the groove opening, and accommodates the built-in electrical cable therein.

10. The imaging module according to claim 8, wherein the built-in electrical cable is a coaxial cable that is configured to include an internal conductor, a primary coating layer coating the internal conductor, an external conductor provided around the primary coating layer, and a secondary coating layer coating the external conductor, and the groove portion is provided with step differences that are along the internal conductor exposed at a front end of the built-in electrical cable, the primary coating layer, and the external conductor.

11. An insulating-tube-attached imaging module comprising:
the imaging module according to claim 1; and
an insulating tube that accommodates the imaging module therein.

12. A lens-attached imaging module comprising
a sleeve-shaped metal frame member that accommodates:
the three-dimensional wiring base and the solid-state image sensing device of the insulating-tube-attached imaging module according to claim 11; and a lens unit fixed to the solid-state image sensing device.

13. An endoscope comprising:
the lens-attached imaging module according to claim 12; and
an insertion portion that accommodates the lens-attached imaging module therein.

14. An imaging module comprising:
an electrical cable;
a solid-state image sensing device having a light-receiving face perpendicular to an axis direction of a front end of the electrical cable; and
a three-dimensional wiring base including a molded product extending in the axis direction, the molded product having a surface on which a wiring is formed, the molded product having a mount surface that is used to package the solid-state image sensing device thereon and is provided on a front end of the molded product, wherein
the mount surface has two opposed apexes which sandwich a central portion therebetween and is molded so that a distance between the two apexes is the longest in distances between two points on sides of the mount surface, a cross section parallel to the mount surface of the three-dimensional wiring base is equal to the mount surface or smaller than the mount surface, and a distance between two points that is the longest in distances on sides of a shape in a plan view of the solid-state image sensing device is equal to or shorter than the distance between the two apexes, and
the surface of the molded product is provided with a groove portion that is used to accommodate the electrical cable therein and extends in an extending direction of the molded product,
the groove portion comprises:
a groove opening that is located on the same plane as the surface of the molded product and has a width smaller than a diameter of the electrical cable; and
an inner groove that is formed inside the groove portion, has a width larger than a width of the groove opening, and accommodates the electrical cable therein.

15. An imaging module comprising:
an electrical cable;
a solid-state image sensing device having a light-receiving face perpendicular to an axis direction of a front end of the electrical cable; and
a three-dimensional wiring base including a molded product extending in the axis direction, the molded product having a surface on which a wiring is formed, the molded product having a mount surface that is used to package the solid-state image sensing device thereon and is provided on a front end of the molded product, wherein
the mount surface has two opposed apexes which sandwich a central portion therebetween and is molded so that a distance between the two apexes is the longest in distances between two points on sides of the mount surface, a cross section parallel to the mount surface of the three-dimensional wiring base is equal to the mount surface or smaller than the mount surface, and a distance between two points that is the longest in distances on sides of a shape in a plan view of the solid-state image sensing device is equal to or shorter than the distance between the two apexes,
the surface of the molded product is provided with a groove portion that is used to accommodate the electrical cable therein and extends in an extending direction of the molded product,
the electrical cable includes a plurality of built-in electrical cables, and
groove portions whose number corresponds to the number of the built-in electrical cables are provided, and
the groove portion comprises:
a groove opening that is located on the same plane as the surface of the molded product and has a width smaller than a diameter of the built-in electrical cable; and
an inner groove that is formed inside the groove portion, has a width larger than a width of the groove opening, and accommodates the built-in electrical cable therein.

16. An imaging module comprising:
an electrical cable;
a solid-state image sensing device having a light-receiving face perpendicular to an axis direction of a front end of the electrical cable; and
a three-dimensional wiring base including a molded product extending in the axis direction, the molded product having a surface on which a wiring is formed, the molded product having a mount surface that is used to package the solid-state image sensing device thereon and is provided on a front end of the molded product, wherein
the mount surface has two opposed apexes which sandwich a central portion therebetween and is molded so that a distance between the two apexes is the longest in distances between two points on sides of the mount surface, a cross section parallel to the mount surface of the three-dimensional wiring base is equal to the mount surface or smaller than the mount surface, and a distance between two points that is the longest in distances on sides of a shape in a plan view of the solid-state image sensing device is equal to or shorter than the distance between the two apexes,
the surface of the molded product is provided with a groove portion that is used to accommodate the electrical cable therein and extends in an extending direction of the molded product,
the electrical cable includes a plurality of built-in electrical cables,
groove portions whose number corresponds to the number of the built-in electrical cables are provided,
the built-in electrical cable is a coaxial cable that is configured to include an internal conductor, a primary coating layer coating the internal conductor, an external conductor provided around the primary coating layer, and a secondary coating layer coating the external conductor, and the groove portion is provided with step differences that are along the internal conductor exposed at a front end of the built-in electrical cable, the primary coating layer, and the external conductor.

* * * * *